(12) United States Patent
Vakkalanka et al.

(10) Patent No.: US 10,786,504 B2
(45) Date of Patent: Sep. 29, 2020

(54) METHOD OF TREATMENT AND COMPOSITIONS COMPRISING A DUAL PI3K DELTA-GAMMA KINASE INHIBITOR AND A CORTICOSTEROID

(71) Applicant: Rhizen Pharmaceuticals SA, La Chaux-de-Fonds (CH)

(72) Inventors: Swaroop K. V. S. Vakkalanka, La Chaux-de-Fonds (CH); Srikant Viswanadha, Hyderabad (IN)

(73) Assignee: Rhizen Pharmaceuticals SA, La Chaux-de-Fonds (CH)

( * ) Notice: Subject to any disclaimer, the term of this patent is extended or adjusted under 35 U.S.C. 154(b) by 0 days.

(21) Appl. No.: 15/508,429

(22) PCT Filed: Sep. 3, 2015

(86) PCT No.: PCT/IB2015/056720
§ 371 (c)(1),
(2) Date: Mar. 2, 2017

(87) PCT Pub. No.: WO2016/035032
PCT Pub. Date: Mar. 10, 2016

(65) Prior Publication Data
US 2017/0281630 A1    Oct. 5, 2017

(30) Foreign Application Priority Data
Sep. 3, 2014   (IN) .......................... 4287/CHE/2014

(51) Int. Cl.
| | | |
|---|---|---|
| A61K 31/519 | (2006.01) | |
| A61K 31/573 | (2006.01) | |
| A61K 45/06 | (2006.01) | |
| A61K 31/56 | (2006.01) | |

(52) U.S. Cl.
CPC ............ *A61K 31/519* (2013.01); *A61K 31/56* (2013.01); *A61K 31/573* (2013.01); *A61K 45/06* (2013.01)

(58) Field of Classification Search
CPC .............................. A61K 31/519; A61K 31/573
See application file for complete search history.

(56) References Cited

U.S. PATENT DOCUMENTS

| | | | |
|---|---|---|---|
| 4,511,289 A | 4/1985 | Herron | |
| 2011/0118257 A1 | 5/2011 | Muthuppalaniappan et al. | |
| 2012/0289496 A1 | 11/2012 | Nagarathnam et al. | |
| 2013/0039928 A1* | 2/2013 | Biswal | A61K 31/00 424/172.1 |

FOREIGN PATENT DOCUMENTS

| | | |
|---|---|---|
| CA | 2872252 A1 | 11/2013 |
| CN | 204282361 U | 4/2015 |
| GB | 1578446 A | 11/1980 |
| WO | WO-2006005611 A2 | 1/2006 |
| WO | WO-2009088986 A1 | 7/2009 |
| WO | WO-2009088990 A1 | 7/2009 |
| WO | WO-2011008302 A1 | 1/2011 |
| WO | WO-2011029547 A2 | 3/2011 |
| WO | WO-2011-055215 | 5/2011 |
| WO | WO-2012097000 A1 | 7/2012 |
| WO | WO-2012123482 A2 | 9/2012 |
| WO | WO-2012151525 A1 | 11/2012 |
| WO | WO-2014072937 A1 | 5/2014 |

OTHER PUBLICATIONS

RxList webpage for dexamethasone (revised Sep. 2007, retrieved Jan. 18, 2018) (Year: 2007).*
To et al., Targeting Phosphoinositide-3-Kinase-d with Theophylline Reverses Corticosteroid Insensitivity in Chronic Obstructive Pulmonary Disease, Am J Respir Crit Care (Year: 2010).*
International Search Report issued in PCT/IB2015/056720 dated Nov. 17, 2015.
To, et al., Targeting Phosphoinositide-3-Kinase-δ With Theophylline Reverses Corticosteroid Insensitvity in Chronic Obstructive Pulmonary Disease, Am. J. Respir. Crit. Care. Med., 2010, 182:897-904.
Ito, et al,. Therapeutic Potential of Phosphatidylinositol 3-Kinase Inhibitors in Inflammatory Respiratory Disease, JPET, 2007, 321(1):1-8.

* cited by examiner

*Primary Examiner* — Sarah Pihonak
*Assistant Examiner* — Jason Deck
(74) *Attorney, Agent, or Firm* — Blank Rome LLP

(57) ABSTRACT

This present disclosure relates to a method of treating autoimmune, respiratory and/or inflammatory diseases or conditions, e.g., asthma, COPD, rheumatoid arthritis and idiopathic Pulmonary Fibrosis (IPF). The method comprises administering a dual PI3K delta and gamma inhibitor and a corticosteroid. The present invention also relates to pharmaceutical compositions containing a dual PI3K delta and gamma inhibitor and a corticosteroid.

31 Claims, 6 Drawing Sheets

(*p<0.05)

(*p<0.05)

METHOD OF TREATMENT AND COMPOSITIONS COMPRISING A DUAL PI3K DELTA-GAMMA KINASE INHIBITOR AND A CORTICOSTEROID

The present application is a national stage of International Patent Application No. PCT/IB2015/056720, filed Sep. 3, 2015, which claims the benefit of Indian Patent Application No. 4287/CHE/2014, filed Sep. 3, 2014, which is hereby incorporated by reference in its entirety.

FIELD OF THE INVENTION

The present invention relates to a method of treating autoimmune, respiratory and/or inflammatory diseases and conditions comprising administering to a patient in need thereof a dual PI3K delta/gamma inhibitor and at least one corticosteroid. In preferred embodiments, the method relates to the treatment of psoriasis, rheumatoid arthritis, idiopathic pulmonary fibrosis (IPF), asthma, chronic obstructive pulmonary disease (COPD), and any combination thereof.

BACKGROUND OF THE INVENTION

Autoimmune, respiratory and inflammatory diseases such as rheumatoid arthritis (RA), idiopathic pulmonary fibrosis (IPF), psoriasis, systemic lupus erythematosus (SLE), COPD and asthma are chronic and often progressive diseases associated with a dysregulated or an overactive immune system, respectively. The causes and the drivers of these diseases remain ill defined. They are typically characterized by complex cellular interactions between multiple inflammatory cells of the innate and adaptive immune system. Accordingly, the heterogeneity and complexity of the disease etiology of these conditions makes the search for new appropriate cellular targets challenging, as it is unclear who in the cellular infiltrate is a primary player of the pathology versus an "innocent" bystander. Therefore, targeting signalling molecules that are required for the activation of multiple immune cells may be the more likely route to success in combating these chronic, immune cell mediated diseases.

Rheumatoid arthritis (RA) is a progressive, systemic autoimmune disease characterized by chronic inflammation of multiple joints with associated systemic symptoms such as fatigue. This inflammation causes joint pain, stiffness and swelling, resulting in loss of joint function due to destruction of the bone and cartilage, often leading to progressive disability. Patients with RA also have an increased likelihood of developing other systemic complications such as osteoporosis, anaemia, and others affecting the lungs and skin.

RA is one of the most common forms of autoimmune disease and affects over 21 million people worldwide. Rheumatoid arthritis has a worldwide distribution with an estimated prevalence of 1 to 2%. Prevalence increases with age, approaching 5% in women over the age of 55. The average annual incidence in the United States is about 70 per 100,000 annually. Both incidence and prevalence of rheumatoid arthritis are two to three times greater in women than in men. Although rheumatoid arthritis may present at any age, patients most commonly are first affected in the third to sixth decades. RA is known to impact quality of life, causing not only physical problems but also significant negative impact on quality of life. RA also impacts on the average life expectancy, shortening it by three to seven years. After 10 years, less than 50% of patients with RA can work or function normally on a day-to-day basis. RA is also been reported to lead to an economic burden on national economies due to hospital admissions, health care costs and lost productivity. RA is the cause of over nine million primary care physician visits in the UK annually, representing £833 million in lost production. It is also estimated to have cost the UK economy £5.5 billion in 2000. In the US, experts have estimated that RA costs more to business and industry than any other disease, with 500,000 hospitalizations per year and the burden of illness on the economy for arthritis (as a whole) is estimated to be $128 billion.

There are a number of treatments available to manage RA. Some address the signs and symptoms of RA, others aim to modify the course of the disease and positively impact the systemic effects of RA, such as fatigue and anaemia.

The current treatments include, for example, use of:
Biologics: These are genetically-engineered drugs that target specific cell surface markers or messenger substances in the immune system called cytokines, which are produced by cells in order to regulate other cells during an inflammatory response. An example of a specific cytokine targeted by biologics is tumor necrosis factor alpha (TNFα).
Traditional disease-modifying anti-rheumatic drugs (DMARDs): These are non-specific immunosuppressive drugs, which are intended to combat the signs and symptoms of RA as well as slowing down progressive joint destruction. These treatments are often used in combination with one another, or in combination with a biologic agent, to improve patient response
Glucocorticoids (corticosteroids): These are anti-inflammatory drugs related to cortisol—a steroid produced naturally in the body—that work by countering inflammation. However, the side-effects of glucocorticoids, which include hyperglycemia, osteoporosis, hypertension, weight gain, cataracts, sleep problems, muscle loss, and susceptibility to infections, limits their use
Non-steroidal anti-inflammatory drugs (NSAIDs): These manage the signs and symptoms of RA, such as reducing pain, swelling, and inflammation, but do not alter the course of the disease or slow the progression of joint destruction There are also a number of RA therapies targeting other components of the immune system. These include biologic treatments targeting alternative cytokines such as interleukin-6 (IL-6) that help to reduce inflammation and the progression of RA in the joints and throughout the body.

Asthma is the most common chronic disease among children and also affects millions of adults. Some 235 million people worldwide suffer from this disease. The causes of asthma are not well understood, but effective medicines are available that can treat it, thus largely avoiding the diminished lives, disabilities and death it can bring. Unfortunately, for many people with asthma, particularly the poor, these effective treatments are too costly or not available at all.

Chronic obstructive pulmonary disease (COPD) is a highly prevalent condition and a major cause of morbidity and mortality worldwide. As the disease progresses, patients with COPD may become prone to frequent exacerbations, resulting in patient anxiety, worsening health status, lung function decline, and increase in mortality rate. These episodes of worsening respiratory function lead to increases in health care utilization, hospital admissions and costs. Worse, frequent exacerbations are associated with a faster decline in lung function, thereby shortening life expectancy.

According to the recommendations of Global Initiative for Chronic Obstructive Lung Disease (GOLD), the first line therapy for COPD are long acting (3-agonists, long acting muscarinic antagonists and inhalation corticosteroids. However, these drugs reduce the symptoms and exacerbations associated with the disease rather than targeting its molecular and cellular basis. Accordingly, there is still a need for further improvement of COPD therapy.

Phosphoinositide-3 kinase (PI3K) belongs to a class of intracellular lipid kinases that phosphorylate the 3 position hydroxyl group of the inositol ring of phosphoinositide lipids (PIs) generating lipid second messengers. While alpha and beta isoforms are ubiquitous in their distribution, expression of delta and gamma is restricted to circulating hematogenous cells and endothelial cells. Unlike PI3K-alpha or beta, mice lacking expression of gamma or delta do not show any adverse phenotype indicating that targeting of these specific isoforms would not result in overt toxicity.

Recently, targeted inhibitors of the phosphoinositide-3-kinase (PI3K) pathway have been suggested as immunomodulatory agents. This interest stems from the fact that the PI3K pathway serves multiple functions in immune cell signalling, primarily through the generation of phosphatidylinositol (3,4,5)-trisphosphate (PIP3), a membrane bound second messenger. PIP3 recruits proteins to the cytoplasmic side of the lipid bilayer, including protein kinases and GTPases, initiating a complex network of downstream signalling cascades important in the regulation of immune cell adhesion, migration, and cell-cell communication.

The four class I PI3K isoforms differ significantly in their tissue distribution. PI3Kα and PI3Kβ are ubiquitous and activated downstream of receptor tyrosine kinases (RTK), whereas PI3Kδ and PI3Kγ are primarily limited to hematopoietic and endothelial cells, and are activated downstream of RTKs, and G protein coupled receptors (GPCR), respectively. Mouse genetic studies have revealed that PI3Kα and PI3Kβ are essential for normal development, whereas loss of PI3Kδ and/or PI3Kγ yields viable offspring with selective immune deficits The expression pattern and functions of PI3Kδ and PI3Kγ have generated much interest in developing PI3K δ/γ inhibitors as agents for many diseases, including rheumatoid arthritis, allergies, asthma, chronic obstructive pulmonary disease and multiple sclerosis (Hirsch et al., *Pharmacol. Ther.*, 118, 192-205 2008; Marone et al., Biochim. Biophys. Acta., 1784, 159-185. 2008; Rommel et al., *Nat. Rev. Immunol.*, 7, 191-201., 2007; Ruckle et al., *Nat. Rev. Drug Discov.*, 5, 903-918.2006). Studies using both pharmacologic and genetic methods have shown these two isoforms often demonstrate synergistic interactions with each other (Konrad et al., *J. Biol. Chem.*, 283, 33296-33303, 2008; Laffargue et al., *Immunity*, 16, 441-451, 2002).

In mast cells, for example, PI3Kδ is essential for degranulation in response to IgE cross-linking of Fc-receptors (Ali et al., *J. Immunol.*, 180, 2538-2544. 2008), but PI3Kγ plays an important role in amplifying the response (Laffargue et al., *Immunity*, 16, 441-451 2002). Similar effects have been seen in other cellular functions, including lymphocyte homing and the neutrophil respiratory burst where PI3Kγ plays a critical role and PI3Kδ amplifies each process. The nonredundant but related roles of PI3Kδ and PI3Kγ have made it difficult to determine which of the two isoforms (alone or in combination) is best targeted in a particular inflammatory disorder. Studies using mice that lack PI3Kδ and/or PI3Kγ or express kinase-dead variants of PI3Kδ and PI3Kγ have been valuable tools in understanding their roles. For example, PI3Kδ knockout mice demonstrated diminished neutrophil chemotaxis, diminished antibody production (both T cell dependent and independent) (Jou et al., *Mol. Cell. Biol.*, 22, 8580-8591. 2002), and lower numbers of mature B cells (Clayton et al., *J. Exp. Med.*, 196, 753-763. 2002; Jou et al., *Mol. Cell. Biol.*, 22, 8580-8591. 2002) and a decrease in their proliferation in response to anti-IgM (Jou et al., *Mol. Cell. Biol.*, 22, 8580-8591. 2002). This phenotype was replicated in the PI3Kδ kinase-dead variant and with PI3Kδ selective inhibitors along with decreased numbers of and proliferation of mast cells, and an attenuated allergic response. The PI3Kγ knockout contained higher numbers of, but less responsive, neutrophils, lower numbers of and less responsive macrophages and dendritic cells displayed decreased mast cell degranulation ((Laffargue et al., *Immunity*, 16, 441-451 2002), a higher ratio of CD4+ to CD8+ T cells), increased thymocyte apoptosis, diminished induction of CXCR3 on activated T cells and decreased cardiac contractility. This latter effect on cardiac tissue was a concern for chronic dosing of patients with PI3Kγ inhibitors. However, this concern was largely mitigated when the PI3Kγ kinase-dead variant (which better mimics inhibition of the kinase rather than loss of the protein) showed similar immune cell phenotypes, but importantly had no cardiac defects. The cardiac effect was later shown to be due to scaffolding effects rather than the catalytic activity of PI3Kγ. The dual PI3Kδ/PI3Kγ knockout was viable but exhibited serious defects in T cell development and thymocyte survival. The PI3Kγ knockout/PI3Kδ kinase-dead combination produced a similar phenotype suggesting that at least within the immune system, the role of PI3Kδ is likely only a catalytic one. Interpretation of studies using knockout and kinase-dead mice can be challenging because these models provide only a steady-state picture of the immune system, lack temporal and dose control, and do not permit a full understanding of how a dynamic immune response will react to reversible inhibition. Selective inhibitors with varying profiles (PI3Kδ, PI3Kγ, and PI3K δ/γ) are necessary for studies of leukocyte signalling in order to assess the relative contributions of each PI3K to immune cell activation. (see Olusegon et al., *Chemistry & Biology*, 1, 123-134 including the cited references therein).

Dual inhibition of PI3K δ/γ is strongly implicated as an intervention strategy in allergic and non-allergic inflammation of the airways and other autoimmune diseases. Scientific evidence for PI3K-δ and γ gamma involvement in various cellular processes underlying asthma and COPD stems from inhibitor studies and gene-targeting approaches. Also, resistance to conventional therapies such as corticosteroids in several COPD patients has been attributed to an up-regulation of the PI3K δ/γ pathway. Disruption of PI3K δ/γ signalling therefore provides a novel strategy aimed at counteracting the immuno-inflammatory response. Due to the pivotal role played by PI3K δ and γ in mediating inflammatory cell functionality such as leukocyte migration and activation, and mast cell degranulation, blocking these isoforms may also be an effective strategy for the treatment of rheumatoid arthritis as well. Given the established criticality of these isoforms in immune surveillance, inhibitors specifically targeting the delta and gamma isoforms would be expected to attenuate the progression of immune response encountered in airway inflammation and rheumatoid arthritis. Given the established criticality of these isoforms in immune surveillance, inhibitors specifically targeting the δ and γ isoforms would be expected to attenuate the progression of immune response encountered in airway inflammation and rheumatoid arthritis (William et al., *Chemistry & Biology*, 17:123-134, 2010; and Thompson, et al., *Chemistry*

& *Biology*, 17:101-102, 2010) Reviews and studies regarding PI3K and related protein kinase pathways have been given by Pixu Liu et. al. (*Nature Reviews Drug Discovery*, 2009, 8, 627-644); Nathan T. et. al., *Mol Cancer Ther.*, 2009; 8 (1) January, 2009); Romina Marone et al., *Biochimica et Biophysica Acta.*, 1784 (2008) 159-185) and B. Markman et al., *Annals of Oncology, Advance Access* published August 2009). Similarly reviews and studies regarding role of PI3K δ and γ have been given by William et al., *Chemistry & Biology*, 17:123-134, 2010 and Timothy et al., *J Med. Chem.*, Web Publication Aug. 27, 2012. All of these literature disclosures are incorporated herein as reference in their entirety for all purposes.

Recent developed compounds, such as IPI-145 and CAL130 have been reported as dual inhibitors of PI3K δ/γ. IPI-145 is under clinical investigation for cancer as well as for asthma. There are currently no reports of CAL-130 being investigated for any clinical purpose.

Additional reference is made herein to International Patent Application Nos. PCT/IB2010/002804, filed Nov. 3, 2010, and PCT/US2012/36594, filed May 4, 2012; U.S. patent application Ser. No. 12/938,609, filed Nov. 3, 2010, and Ser. No. 13/464,587 filed May 4, 2012 as well to the compounds as disclosed in International Publication Nos. WO 2009/088986, WO 2009/088990, WO 2011/008302 and WO 2012/097000, each of which is incorporated herein by reference in its entirety for all purposes.

Corticosteroids are potent anti-inflammatory agents, able to decrease the number, activity and movement of inflammatory cells. Corticosteroids are commonly used to treat a wide range of chronic and acute inflammatory conditions including asthma, chronic obstructive pulmonary disease (COPD), allergic rhinitis, rheumatoid arthritis, inflammatory bowel disease and autoimmune diseases. Corticosteroids mediate their effects through the glucocorticoid receptor (GR). The binding of corticosteroids to GR induces its nuclear translocation which, in turn, affects a number of downstream pathways via DNA-binding-dependent (e.g. transactivation) and -independent (e.g. transexpression) mechanisms.

Corticosteroids for treating chronic inflammatory conditions in the lung (such as asthma and COPD) are currently administered through inhalation. One of the advantages of employing inhaled corticosteroids (ICS) is the possibility of delivering the drug directly to the site of action, thereby limiting systemic side-effects, and resulting in a more rapid clinical response and higher therapeutic ratio.

Although ICS treatment can afford important benefits, especially in asthma, it is important to minimize ICS systemic exposure, which leads to the occurrence and severity of unwanted side effects that may be associated with chronic administration. Moreover, the limited duration of action of ICS currently available in the clinical practice contributes to suboptimal management of the disease. While inhaler technology is an important point to target the lung, the modulation of the substituents on the corticosteroids molecular scaffold is important for the optimization of pharmacokinetic and pharmacodynamic properties in order to decrease oral bioavailability, confine pharmacological activity only in the lung (prodrugs and soft drugs) and increase systemic clearance. Moreover, long lasting ICS activity in the lung is highly desirable as once daily administration of ICS would allow the reduction of the frequency of administration and, thus, substantially improve patient compliance and, as a result, disease management and control. In sum, there is a pressing medical need for developing ICS with improved pharmacokinetic and pharmacodynamic characteristics.

Glucocorticoids isoxazolidine derivatives are described, for example, in WO 2006/005611, GB 1,578,446 and in "Synthesis and topical anti-inflammatory activity of some steroidal [16α,17α-d] isoxazolidines", M. J. Green et al., *J. Med. Chem.*, 25, 1492-1495, 1982, each of which is incorporated herein by reference in their entireties. Additional glucocorticoid isoxazolidine derivatives are also described in WO 2011/029547 and WO 2012/123482.

Despite currently available intervention therapies, autoimmune disorders such as RA, psoriasis and respiratory disorders such as asthma and COPD remains disease classes with a significant unmet medical need.

Accordingly, it is an objective of the present invention to provide methods and pharmaceutical compositions for the treatment of respiratory and/or inflammatory diseases and conditions having enhanced activity. The pharmaceutical compositions allow for treating autoimmune, respiratory and inflammatory diseases and conditions with a smaller amount of active compound(s) and/or allow for treating autoimmune, respiratory and inflammatory diseases and conditions in a more efficient way, thereby minimizing or obviating possibly existing adverse effects generally linked to any kind of treatment with an active compound in high doses and/or for a longer period of time.

As described herein, the objective may be achieved by combining drugs affecting two diverse yet complimentary pathways, in order to be efficacious at lower doses compared to that of either inhibitor alone. Thus, the present invention provides an effective approach of combining the two different signalling pathways which hold significant therapeutic potential when combined together. In particular the combination is therapeutically beneficial in lowering the required therapeutically effective concentration of either or both the corticosteroid and the dual PI3K delta-gamma inhibitor.

SUMMARY OF THE INVENTION

The present invention relates to a pharmaceutical composition comprising a PI3K delta and gamma dual inhibitor and at least one corticosteroid, and to the use of such a pharmaceutical composition for treating autoimmune, respiratory and inflammatory diseases and conditions.

One embodiment is a pharmaceutical composition comprising a PI3K delta and gamma dual inhibitor and at least one corticosteroid.

Another embodiment is a method of treating a patient suffering from an autoimmune, respiratory and/or inflammatory disease or condition comprising administering to the patient a PI3K delta and gamma dual inhibitor and at least one corticosteroid. In one preferred embodiment, the PI3K delta and gamma dual inhibitor and at least one corticosteroid are administered together in a single pharmaceutical composition. In one preferred embodiment, the disease or condition is idiopathic pulmonary fibrosis (IPF), asthma, rheumatoid arthritis (RA) or COPD.

Yet another embodiment is the use of a combination of a PI3K delta and gamma dual inhibitor and at least one corticosteroid for the treatment in a patient of an autoimmune, respiratory and/or inflammatory disease or condition, such as for the treatment of asthma, RA or COPD.

In a preferred embodiment, the PI3K delta and gamma dual inhibitor is a compound of formula A (shown below) or a pharmaceutically acceptable salt thereof.

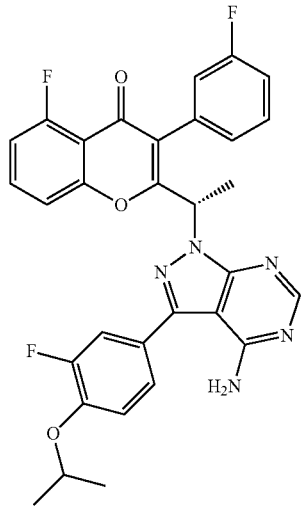

Formula A

Suitable corticosteroids include, but are not limited to dexamethasone, betamethasone, prednisolone, methyl prednisolone, prednisone, hydrocortisone, fluticasone, triamcinolone, cortisone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate, hydrocortisone probutate, and pharmaceutically acceptable salts thereof.

In a preferred embodiment, the corticosteroids are selected from dexamethasone, betamethasone, prednisolone, methyl prednisolone, prednisone, hydrocortisone, fluticasone, triamcinolone, budesonide, cortisone, and any combination of any of the foregoing.

One embodiment is a pharmaceutical composition comprising a compound of formula A or a pharmaceutically acceptable salt thereof, and a corticosteroid. In one preferred embodiment, the pharmaceutical composition comprises a therapeutically effective amount of a compound formula A or a pharmaceutically acceptable salt thereof, and a therapeutically effective amount of a corticosteroid (for example, for treating asthma, RA, or COPD).

Another embodiment is a method of treating an autoimmune, respiratory and/or inflammatory disease or condition, such as asthma, RA or COPD, comprising administering to a patient in need thereof a compound of formula A:

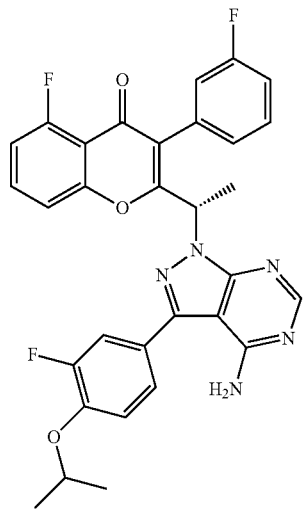

Formula A or a pharmaceutically acceptable salt thereof and a corticosteroid. In one preferred embodiment, the compound of formula A or a pharmaceutically acceptable salt thereof and at least one corticosteroid are administered together in a single pharmaceutical composition. In one embodiment, the disease or condition is asthma. In another embodiment, the disease or condition is RA. In yet another embodiment, the disease or condition is COPD.

Yet another embodiment is a method of treating a patient suffering from an autoimmune, respiratory and/or inflammatory disease or condition, such as asthma, RA, or COPD, comprising administering to the patient a compound of formula A or a pharmaceutically acceptable salt thereof, and a corticosteroid selected from dexamethasone, betamethasone, prednisolone, methyl prednisolone, prednisone, hydrocortisone, fluticasone, triamcinolone, budesonide or cortisone, and any combination thereof. In one preferred embodiment, the compound of formula A or a pharmaceutically acceptable salt thereof and at least one corticosteroid are administered together in a single pharmaceutical composition.

DETAILED DESCRIPTION OF THE INVENTION

Figure 1A:
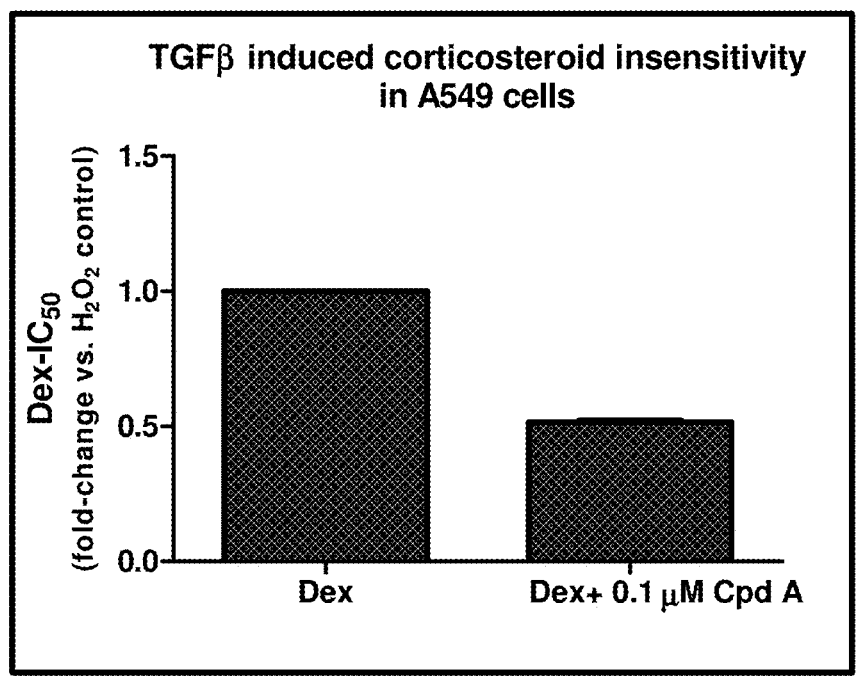
FIG. 1A is a bar graph depicting the effect of compound A on the $IC_{50}$ of dexamethasone (Dex) in TGF-β1 treated A549 cells according to the procedure in Example 1.

In one aspect, the method of combining a dual PI3K delta and gamma inhibitor (such as a compound of formula A, or a pharmaceutically acceptable salt thereof) with a corticosteroid, as described in any of the embodiments herein, exhibits an activity (i.e., a synergistic activity) which is significantly higher than the activity expected based on the individual activities of each of the dual PI3K delta and gamma inhibitor or the corticosteroid alone.

In another aspect, the method of combining a dual PI3K delta and gamma inhibitor (such as a compound of formula A, or a pharmaceutically acceptable salt thereof) with a corticosteroid exhibits an activity even when the corticosteroid alone is insensitive as a single agent.

Thus, the methods described herein allow for treating autoimmune, respiratory and inflammatory diseases and conditions with a smaller amount of active compound(s) and/or allow for treating autoimmune, respiratory and inflammatory diseases and conditions for a longer period of time in a more efficient way.

Another embodiment is a pharmaceutical composition comprising a dual PI3K delta and gamma inhibitor (such as a compound of formula A, or a pharmaceutically acceptable salt thereof) with a corticosteroid, for use in the treatment of an autoimmune, respiratory and/or inflammatory disease or condition.

Yet another embodiment is a method of treating an autoimmune, respiratory and/or inflammatory disease or condition comprising administering to a patient in need thereof a therapeutically effective amount of a pharmaceutical composition according to the present invention.

Yet another embodiment is the use of a pharmaceutical composition according to any of the embodiments described herein for making a medicament useful for treating an autoimmune, respiratory and/or inflammatory disease or condition.

In the pharmaceutical compositions described herein, the PI3K delta and gamma dual inhibitor (such as a compound of formula A, or a pharmaceutically acceptable salt thereof) may be in a form selected from solvates, hydrates and/or salts with pharmacologically acceptable acids or bases.

In the pharmaceutical compositions described herein, the corticosteroid may be in a form selected from solvates, hydrates or salts with pharmacologically acceptable acids or bases.

Yet another embodiment is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, or a renal disease or disorder. The method includes administering an effective amount of one or more compositions of the present invention.

Examples of immune disorders which can be treated by the methods and compositions described herein include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, Idiopathic pulmonary fibrosis (IPF), chronic relapsing hepatitis, primary biliary cirrhosis, allergic conjunctivitis and atopic dermatitis.

Pharmaceutically acceptable salts, as described herein, include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; salts of chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as MeI (methyl iodide) and $(Me)_2SO_4$; salts of non-natural amino acids such as D-isomers or substituted amino acids; salts of guanidine; and salts of substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; PI=phosphatidylinositol.

Abbreviations used herein have their conventional meaning within the chemical and biological arts, unless otherwise indicated.

The term "effective amount" or "therapeutically effective amount" refers to that amount of a compound described herein that is sufficient to effect the intended application including, but not limited to, disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal, such as a mammal, for example a human. The methods described herein can be useful in both human therapeutics and veterinary applications. In some embodiments, the patient is a mammal, and in some embodiments, the patient is human. For veterinary purposes, the term "subject" and "patient" include, but are not limited to, farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

The term "selective inhibition" or "selectively inhibit" as applied to a biologically active agent refers to the agent's ability to selectively reduce the target signaling activity as compared to off-target signaling activity, via direct or indirect interaction with the target.

As used herein, the term "dual PI3-kinase Delta (δ) and Gamma (γ) inhibitor" generally refers to a compound that inhibits the activity of both the PI3-kinase δ and γ isozyme more effectively than other isozymes of the PI3K family. A PI3-kinase δ and γ dual inhibitor compound is therefore more selective for PI3-kinase δ and γ than conventional PI3K inhibitors such as CAL-130, wortmannin and LY294002, which are "nonselective PI3K inhibitors." Examples of "dual PI3-kinase Delta (δ) and Gamma (γ) inhibitor" include, but are not limited to, compounds such as IPI-145, and the compounds disclosed in International Patent Application Nos. PCT/IB2010/002804, filed Nov. 3, 2010, and PCT/US2012/36594, filed May 4, 2012; U.S. patent application Ser. No. 12/938,609, filed Nov. 3, 2010, and Ser. No. 13/464,587 filed May 4, 2012 and to compounds disclosed in International Publication Nos. WO 2009/088986, WO 2009/088990, WO 2011/008302 and WO 2012/097000, each of which is incorporated herein by reference in its entirety for all purposes.

For instance, the Dual PI3-kinase δ and γ selective inhibitor may refer to a compound that exhibits a 50% inhibitory concentration ($IC_{50}$) with respect to the delta and gamma type I PI3-kinase that is at least 10-fold, at least 20-fold, at least 50-fold, or at least 100-fold lower than the inhibitor's $IC_{50}$ with respect to the other types of PI3 kinases (i.e., alpha and beta).

Inhibition of PI3-kinase δ and γ may be of therapeutic benefit in treatment of various conditions, e.g., conditions characterized by an inflammatory response including but not limited to autoimmune diseases, allergic diseases, and arthritic diseases. Importantly, inhibition of PI3-kinase δ and γ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, non-infectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defence system as well as conditions associated with reactions of the non-specific defence system.

The therapeutic methods of the invention include methods for the treatment of conditions associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including, but not limited to, monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents.

"Transplant rejection" as used herein refers to an immune response directed against grafted tissue (including organs or cells (e.g., bone marrow), characterized by a loss of function of the grafted and surrounding tissues, pain, swelling, leukocytosis, and thrombocytopenia).

"Allergic disease" as used herein refers to any symptoms, tissue damage, or loss of tissue function resulting from allergy.

"Arthritic disease" as used herein refers to any disease that is characterized by inflammatory lesions of the joints attributable to a variety of etiologies.

"Dermatitis" as used herein refers to any of a large family of diseases of the skin that are characterized by inflammation of the skin attributable to a variety of etiologies.

One embodiment is a pharmaceutical composition comprising a dual PI3K delta and gamma inhibitor (such as a compound of formula A, or a pharmaceutically acceptable salt thereof) and at least one corticosteroid and optionally one or more pharmaceutically acceptable carriers or excipients.

In one embodiment, the pharmaceutical composition includes a therapeutically effective amount of a dual PI3K delta and gamma inhibitor (such as a compound of formula A, or a pharmaceutically acceptable salt thereof) and at least one corticosteroid, and optionally one or more pharmaceutically acceptable carriers or excipients. The pharmaceutical composition may include one or more additional active ingredients as described herein.

The pharmaceutical carriers and/or excipients may be selected from diluents, fillers, salts, disintegrants, binders, lubricants, glidants, wetting agents, controlled release matrices, colorants, flavorings, buffers, stabilizers, solubilizers, and combinations thereof.

The pharmaceutical compositions of the present invention can be administered alone or in combination with one or more other active agents. Where desired, the subject compounds and other agent(s) may be mixed into a preparation or both components may be formulated into separate preparations to use them in combination separately or at the same time.

The dual PI3K delta and gamma inhibitor and the corticosteroid can be administered together or in a sequential manner with one or more other active agents. Where desired, the subject compounds and other agent(s) may be co-administered or both components may be administered in a sequence to use them as a combination.

The compounds and pharmaceutical compositions of the present invention can be administered by any route that enables delivery of the compounds to the site of action, such as orally, intranasally, topically (e.g., transdermally), intraduodenally, parenterally (including intravenously, intraarterially, intramuscularally, intravascularally, intraperitoneally or by injection or infusion), intradermally, by intramammary, intrathecally, intraocularly, retrobulbarly, intrapulmonary (e.g., aerosolized drugs) or subcutaneously (including depot administration for long term release e.g., embedded-under the-splenic capsule, brain, or in the cornea), sublingually, anally, rectally, vaginally, or by surgical implantation (e.g., embedded under the splenic capsule, brain, or in the cornea).

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, suppositories, pellets, pills, troches, and lozenges. The type of packaging will generally depend on the desired route of administration. Implantable sustained release formulations are also contemplated, as are transdermal formulations.

The dosing frequency of the compounds may vary. For example, a dual PI3K delta and gamma inhibitor may be administered at a frequency ranging from twice daily to once every three weeks. The corticosteroid may be administered at a frequency ranging from twice daily to once every three weeks.

The amount of the compound to be administered is dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. An effective amount of a compound of the invention may be administered in either single or multiple doses (e.g., twice or three times a day).

In one embodiment, the pharmaceutical compositions described herein comprise from about 0.001 mg to about 1000 mg, such as from about 0.01 mg to about 500 mg or from about 0.010 mg to about 250 mg or from about 0.030 mg to about 125 mg of a dual PI3K delta and gamma inhibitor (such as a compound of formula A, or a pharmaceutically acceptable salt thereof) and/or from about 0.001 mg to about 1000 mg, such as from about 0.01 mg to about 500 mg or from about 0.010 mg to about 250 mg or from about 0.010 mg to about 125 mg or from about 0.030 mg to about 50 mg of at least one corticosteroid.

In one embodiment, the pharmaceutical compositions described herein comprise the dual PI3K delta and gamma inhibitor and the corticosteroid in a ratio of between about 100:1 and about 1:100 by weight, such as between about 50:1 and about 1:50 by weight or between about 1:10 and about 10:1 by weight, or between about 1:5 and about 5:1 by weight.

The term "co-administration," "administered in combination with," and their grammatical equivalents, as used herein, encompasses administration of two or more agents (such as the dual PI3K delta and gamma inhibitor and the corticosteroid) to an animal so that both agents and/or their metabolites are present in the animal at the same time. Co-administration includes simultaneous administration in separate compositions, administration at different times in separate compositions, or administration in a composition in which both agents are present.

The pharmaceutical compositions described herein may contain one or more corticosteroids selected form dexamethasone, betamethasone, prednisolone, methyl prednisolone, prednisone, hydrocortisone, fluticasone, triamcinolone, budesonide or cortisone prednisolone, methylprednisolone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate, and any combination of any of the foregoing.

In certain embodiments, the corticosteroid is selected from dexamethasone, betamethasone, prednisolone, methyl prednisolone, prednisone, hydrocortisone, fluticasone, triamcinolone, budesonide or cortisone, and any combination thereof.

One particular embodiment of the present invention relates to pharmaceutical compositions wherein the corticosteroid is fluticasone.

Another particular embodiment of the present invention relates to pharmaceutical compositions wherein the corticosteroid is budesonide.

Yet another particular embodiment of the present invention relates to pharmaceutical compositions wherein the corticosteroid is prednisolone.

Yet another particular embodiment of the present invention relates to pharmaceutical compositions wherein the corticosteroid is dexamethasone.

A further embodiment of the present invention relates to a method of treating an indication selected from respiratory diseases and conditions such as diseases of the airways and lungs which are accompanied by increased or altered production of mucus and/or inflammatory and/or obstructive diseases of the airways such as acute bronchitis, chronic bronchitis, chronic obstructive bronchitis (COPD), cough, pulmonary emphysema, allergic or non-allergic rhinitis or sinusitis, chronic sinusitis or rhinitis, nasal polyposis, chronic rhinosinusitis, acute rhinosinusitis, asthma, allergic bronchitis, alveolitis, Farmer's disease, hyperreactive airways, bronchitis or pneumonitis caused by infection, e.g. by bacteria or viruses or helminthes or fungi or protozoons or other pathogens, pediatric asthma, bronchiectasis, pulmonary fibrosis, adult respiratory distress syndrome, bronchial and pulmonary edema, bronchitis or pneumonitis or interstitial pneumonitis caused by different origins, e.g. aspiration, inhalation of toxic gases, vapors, bronchitis or pneumonitis or interstitial pneumonitis caused by heart failure, X-rays, radiation, chemotherapy, bronchitis or pneumonitis or interstitial pneumonitis associated with collagenosis, e.g. lupus erythematodes, systemic scleroderma, lung fibrosis, idiopathic pulmonary lung fibrosis (IPF), interstitial lung diseases or interstitial pneumonitis of different origin, including asbestosis, silicosis, M. Boeck or sarcoidosis, granulomatosis, cystic fibrosis or mucoviscidosis, or a-1-antitrypsin deficiency; or selected from inflammatory diseases and conditions such as inflammatory diseases of the gastrointestinal tract of various origins such as inflammatory pseudopolyps, Crohn's disease, ulcerative colitis, inflammatory diseases of the joints, such as rheumatoid arthritis, or allergic inflammatory diseases of the oro-nasopharynx, skin or the eyes, such as atopic dermatitis, seasonal and perenial, chronic uritcaria, hives of unknown cause and allergic conjunctivitis; and in particular selected from asthma, allergic and non-allergic rhinitis, COPD and atopic dermatitis; comprising administering a therapeutically effective amount of a pharmaceutical composition according to the present invention to a patient in need thereof.

A further embodiment of the present invention relates to the use of a pharmaceutical composition according to the present invention for making a medicament for treating respiratory and/or inflammatory diseases and conditions, particularly wherein the respiratory and/or inflammatory diseases or conditions are selected from asthma, allergic and non-allergic rhinitis, COPD and atopic dermatitis.

A further embodiment of the present invention relates to a pharmaceutical composition according to any embodiment herein, for use in the treatment of respiratory and inflammatory diseases and conditions, particularly wherein the respiratory and inflammatory diseases or conditions are selected from asthma, allergic and non-allergic rhinitis, COPD and atopic dermatitis.

The present invention is now further illustrated by means of the following, non-limiting, examples.

EXAMPLES

Provided below are illustrative examples of the combination of a PI3K delta and gamma dual inhibitor and a corticosteroid.

Example 1: TGF-β1 Induced Corticosteroid Insensitivity in A549 Cells

Test Procedure

A549 cells were trypsinized and 2*104 cells per well were seeded in a 96-well plate and incubated at 37° C. and 5% $CO_2$.

Media was removed and 100 µl of serum free media with 0.1 µM of Compound A was added and incubated for 30 min.

50 µl of 3×TGF-β1 in F12K with 0.5% BSA was added such that the final concentration was 400 pM and incubated at 37° C. and 5% $CO_2$ for 4 h.

50 µl of 4× of desired concentrations of dexamethasone (Dex) was added and incubated for 45 min at 37° C. and 5% $CO_2$.

50 µl of 5× concentration of TNF-α was added such that the final concentration was 1 ng/ml to induce IL-8 and incubated for 24 h.

Supernatant was collected and IL-8 was estimated by ELISA.

Cytokine Assay

IL-8 strips were plated with fresh or thawed supernatants and incubated at room temperature for 2 h or overnight at 4° C.

Contents were discarded and strips were washed with 200 µl of wash buffer per well for 15 s for a total of 5 times.

Strips were blotted dry and 100 µl per well of 1× detection antibody was added and incubated at room temperature for 1 h.

Contents were discarded and strips were washed with 200 µl of wash buffer per well for 15 s for a total of 5 times.

Strips were blotted dry and 100 µl per well of 1× Avidin-HRP antibody was added and incubated at room temperature for 30 min.

Contents were discarded and the strips were washed with 200 µl per well of wash buffer for 15 s for a total of 5 times.

100 µl per well of TMB substrate were added and incubated at room temperature for 5-15 min.

Reaction was stopped by adding 50 µl per well of 2N $H_2SO_4$.

Absorbance was read on a plate reader at A450 nm and A570 nm.

% inhibition for Blank subtracted absorbance values were determined based on the control wells. Data was plotted using GraphPad Prism (Version 5.02).

Results

The results are depicted in FIG. 1A. Compound A (Cpd A) decreased the $IC_{50}$ of dexamethasone for IL-8 concentrations in TGF-β1 treated A549 cells indicating significant potentiation of dexamethasone activity.

Example 2: $H_2O_2$ Induced Corticosteroid Insensitivity in U937 Cells

Test Procedure

U937 cells were maintained in RPMI-1640 with 15 mM glutamine. $6*10^6$ cells were taken in T-25 flask with 12 ml of fresh medium and treated with 1 μM of Compound A and incubated at 37° C. and 5% $CO_2$ for 30 min.

$H_2O_2$ was added at a final concentration of 200 μM to the above cells and incubated for 2 h.

Cells were pelleted and resuspended in serum free media and seeded on to a 96-well plate at $0.15*10^6$ cells per well in 100 μl.

50 μl of 3× Dexamethasone at desired concentrations was added and incubated for 45 min.

50 μl of 4× concentration of TNF-α was added such that the final concentration was 10 ng/ml, to induce IL-8 and incubated for 18 h.

Supernatant was collected and IL-8 was estimated by ELISA.

Cytokine Assay

IL-8 strips were plated with fresh or thawed supernatants and incubated at room temperature for 2 h or overnight at 4° C.

Contents were discarded and strips were washed with 200 μl of wash buffer per well for 15 s for a total of 5 times.

Strips were blotted dry and 100 μl per well of 1× detection antibody was added and incubated at room temperature for 1 h.

Contents were discarded and strips were washed with 200 μl of wash buffer per well for 15 s for a total of 5 times.

Strips were blotted dry and 100 μl per well of 1× Avidin-HRP antibody was added and incubated at room temperature for 30 min.

Contents were discarded and the strips were washed with 200 μl per well of wash buffer for 15 s for a total of 5 times.

100 μl per well of TMB substrate were added and incubated at room temperature for 5-15 min.

Reaction was stopped by adding 50 μl per well of 2N $H_2SO_4$.

Absorbance was read on a plate reader at A450 nm and A570 nm.

Results

Figure 1B:
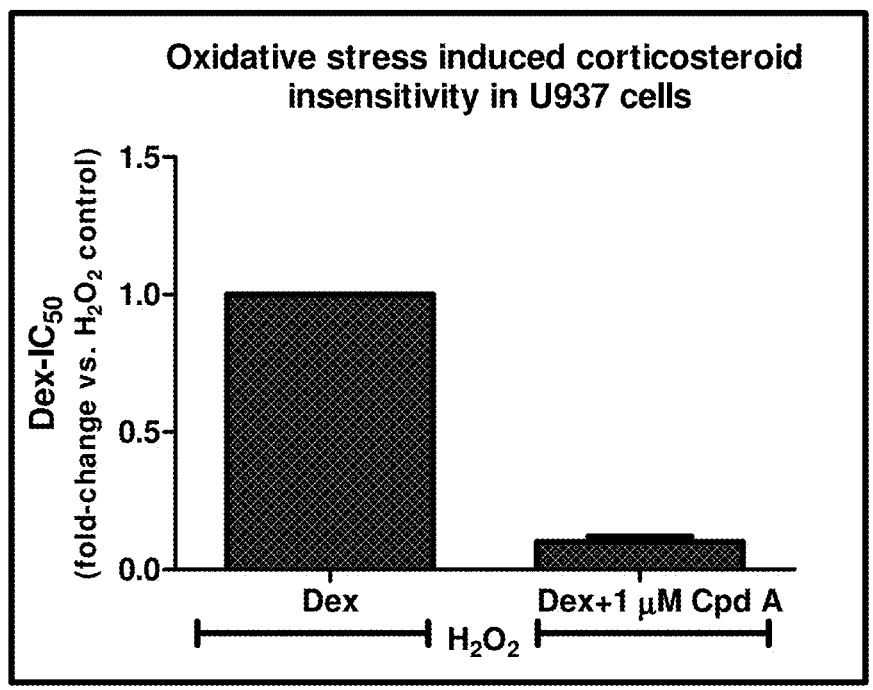
FIG. 1B is a bar graph depicting the effect of compound A on the $IC_{50}$ of dexamethasone (Dex) on IL-8 concentrations in $H_2O_2$ treated U937 cells according to the procedure in Example 2.

As depicted in FIG. 1B, Compound A (Cpd A) decreased the $IC_{50}$ of dexamethasone (Dex) on IL-8 concentrations in $H_2O_2$ treated U937 cells indicating significant potentiation of dexamethasone activity.

Example 3: Chronic Cigarette Smoke Induced Cell Infiltration in Male Balb/c Mice Animals were acclimatized for seven days prior to the start of the experiment. Animals were randomly distributed to various groups based on their body weights. Mice were exposed to the mainstream smoke of 2 cigarettes from day 1 to day 11. Exposure to the smoke of each cigarette lasted for 10 min (each cigarette was completely burned in the first two minutes, followed by an air flow with animal ventilator) and were exposed for the next 20 min with fresh room air. After every second cigarette an additional break of 20 min with exposure to fresh room air was conducted. Control animals were exposed to the room air chamber. Test compound was administered by the intranasal route as suspension from day 12 to day 14 before 30 mins whole body smoke exposure. Mice were exposed to the mainstream smoke of 1 cigarette from day 12 to day 14. On day 15, 24 hours after the last cigarette smoke (CS) exposure animals were exsanguinated under anaesthesia, and the trachea was cannulated and the lungs were lavaged with 0.5 ml aliquots of heparinised PBS (1 unit/ml) four times through tracheal cannula (total volume 2 ml). Bronchioalveolar (BAL) collected was stored at 2-8° C. until assayed for total cell and differential leukocyte count. BAL fluid was centrifuged (500×g for 10 min) and the resulting cell pellet was resuspended in 0.5 ml of heparinised saline. The total number of white blood cells was determined in BAL fluid and blood using a blood cell counter and adjusted to $1×10^6$ cell/ml. Differential cell count was calculated manually. Forty microliters of the cell suspension was centrifuged using cytospin 3 to prepare a cell smear. The cell smear was stained with a blood staining solution for differentiation and microscopically observed by identifying each cell according to its morphological characteristics. The number of each cell type among 300 white blood cells in the cell smear was determined and expressed as a percentage, and the number of neutrophils and macrophages in each BAL fluid were calculated. In addition BAL supernatant were analysed for various cytokinines using ELISA assay.

Figure 2A:
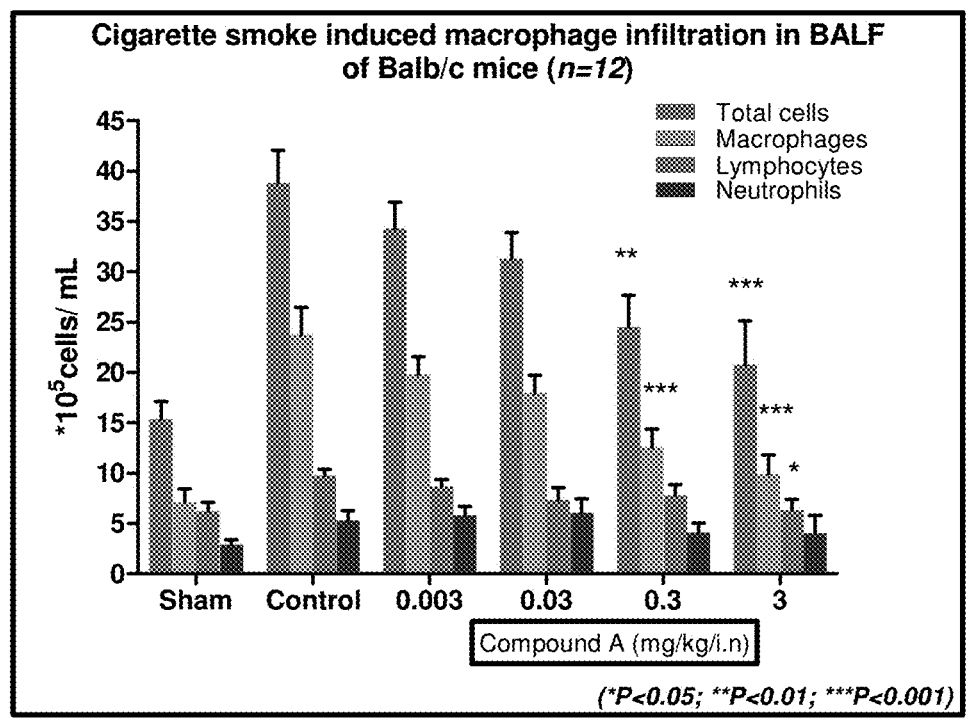
FIG. 2A is a bar graph depicting the effect of compound A on cigarette smoke induced immune cell infiltration in BALF of Balb/c mice according to the procedure in Example 3.
Figure 2B:
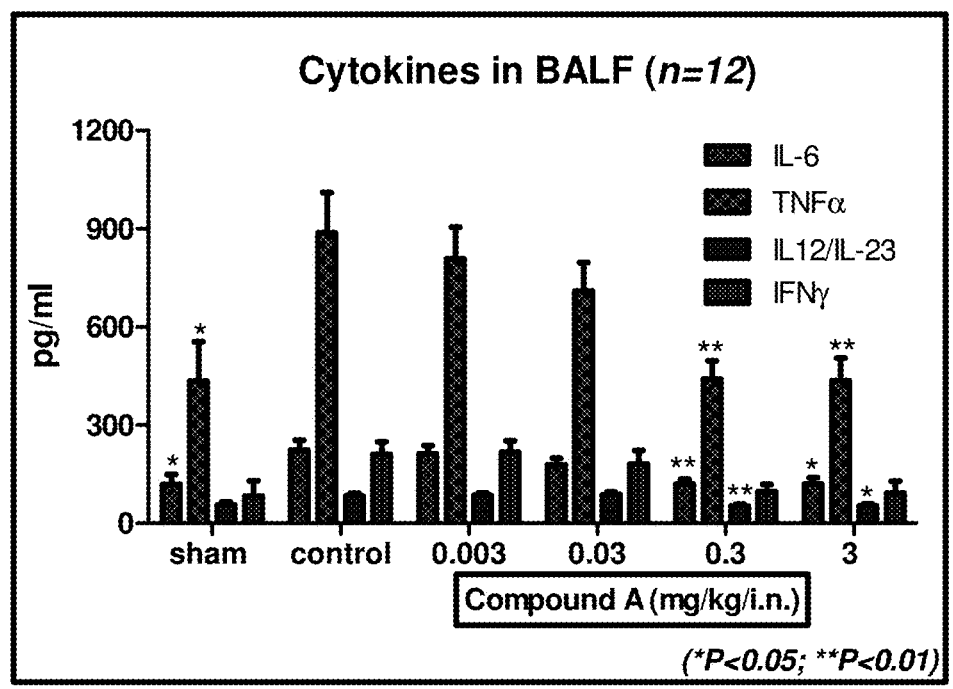
FIG. 2B is a bar graph depicting the effect of compound A on cytokines in BALF according to the procedure in Example 3.

The results are shown in Table 1 and FIGS. 2A and 2B.

All animals survived to the scheduled termination. Compound A showed significant beneficial therapeutic effect in the established murine chronic COPD model as determined by evaluation of cell count in BAL. Macrophage infiltration in BAL fluid with treated animals differed significantly from disease controls with significant reductions (toward normal) of BAL cell count seen in mice treated with Compound A (0.003-3 mg/kg) in a dose dependent manner. Macrophage count was significantly reduced toward normal for mice given 0.003-3 mg/kg Compound A. The percent inhibitions of cytokines are given in Table 1.

TABLE 1

| | Cytokines in BALF (% inhibition) Dose (mg/kg) | | |
|---|---|---|---|
| | 0.003 | 0.03 | 0.3 |
| IL-6 | 11% | 44% | 99% |
| TNFα | 17% | 40% | 99% |
| IL-12/IL-23 | 0% | 0% | 100% |
| IFNγ | 0% | 25% | 90% |

Example 4: Reversal of Corticosteroid Insensitivity in Chronic Cigarette Smoke Induced Cell Infiltration in Male Balb/c Mice Animals were acclimatized for seven days prior to the start of the experiment. Animals were randomly distributed to various groups based on their body weights. Mice were exposed to the mainstream smoke of 2 cigarettes from day 1 to day 11. Exposure to the smoke of each cigarette lasted for 10 min (each cigarette was completely burned in the first two minutes, followed by an air flow with animal ventilator) and were exposed for the next 20 min with fresh room air.

After every second cigarette an additional break of 20 min with exposure to fresh room air was conducted. Control animals were exposed to the room air chamber. Corticosteroid, fluticasone was administered by intranasal route from day 6 to day 11 before 30 mins whole body smoke exposure. Mice were exposed to the mainstream smoke of 1 cigarette from day 12 to day 14. Test compound was administered by the intranasal route as suspension from day 12 to day 14 before 30 mins whole body smoke exposure. On day 15, 24 hours after the last cigarette smoke (CS) exposure animals were exsanguinated under anaesthesia, and the trachea was cannulated and the lungs were lavaged with 0.5 ml aliquots of heparinised PBS (1 unit/ml) four times through tracheal cannula (total volume 2 ml). Bronchioalveolar (BAL) collected was stored at 2-8° C. until assayed for total cell and differential leukocyte count. BAL fluid was centrifuged (500×g for 10 min) and the resulting cell pellet was resuspended in 0.5 ml of heparinised saline. The total number of white blood cells was determined in BAL fluid and blood using a blood cell counter and adjusted to $1\times10^6$ cell/ml. Differential cell count was calculated manually. Forty microliters of the cell suspension was centrifuged using cytospin 3 to prepare a cell smear. The cell smear was stained with a blood staining solution for differentiation and microscopically observed by identifying each cell according to its morphological characteristics. The number of each cell type among 300 white blood cells in the cell smear was determined and expressed as a percentage, and the number of neutrophils and macrophages in each BAL fluid were calculated. In addition BAL supernatant were analysed for various cytokines using ELISA assay.

Figure 3A:
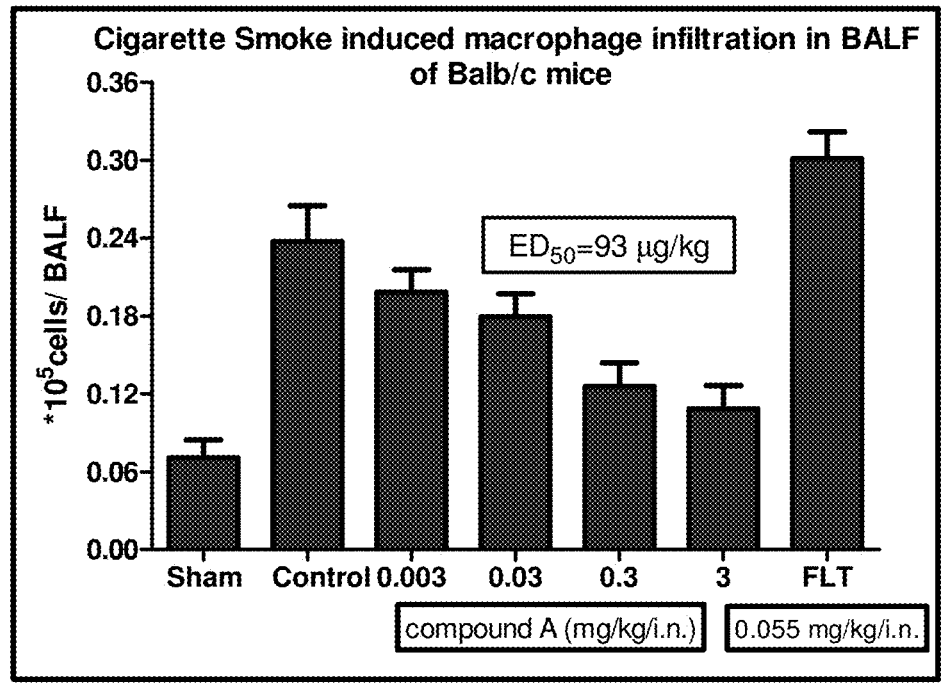
FIG. 3A is a bar graph depicting the effect of compound A and Fluticasone on cigarette smoke induced macrophage infiltration in BALF of Balb/c mice according to the procedure in Example 4.
Figure 3B:
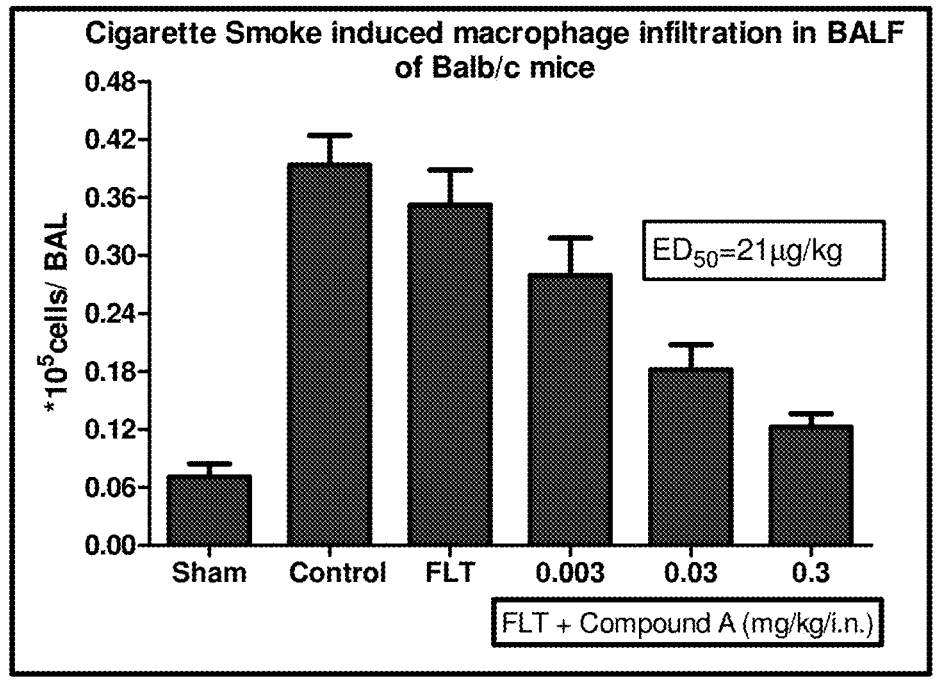
FIG. 3B is a bar graph depicting the effect of combination of compound A and Fluticasone on cigarette smoke induced macrophage infiltration in BALF of Balb/c mice according to the procedure in Example 4.

In combination with fluticasone (FLT), Compound A showed significant beneficial therapeutic effect and reversal of corticosteroid insensitivity by showing a synergistic effect on macrophage infiltration. The $ED_{50}$ of the combination was 0.021 mg/kg in the established murine chronic COPD model as determined by evaluation of cell count in BAL compared to an $ED_{50}$ of 0.093 mg/kg of Compound A alone. The results are also shown in FIGS. 3A and 3B.

Example 5: General Description Related to Patient Identification, Isolation of Neutrophils and Preparation of Cigarette Smoke Extract (CSE) for In-Vitro Testing of Compound A A. Patient Selection Healthy subjects and COPD patients were included for leukocyte experiments. Pulmonary function tests (forced spirometry) and arterial blood gas measurements were performed during the days prior to sampling. According to their spirometry results and smoking habits, patients were classified into two groups: A) Healthy subjects, patients with normal lung function and who did not smoke; B) COPD, patients who had smoked more than 10 pack-years and with airflow obstruction evidenced by a forced expiratory volume in 1 s (FEV1) of <80% predicted and an FEV1 forced vital capacity (FVC) ratio of <70%. Clinical characteristics of the patients are provided in Table 2.

TABLE 2

Table 2: Clinical features.

|  | Healthy (n = 7) | COPD (n = 8) |
|---|---|---|
| Age, yr | 66.1 ± 6 | 65.1 ± 14 |
| Sex (M/F) | 5/2 | 6/2 |
| Tobacco consumption, pack-yr | 0 | 35.2 ± 6 |
| FEV1, % pred | 98 ± 3 | 58.2 ± 3 |
| FVC, % pred | 96 ± 4 | 90.2 ± 6 |
| FEV1/FVC % | 98 ± 3 | 59.1 ± 6 |
| GOLD 1 (mild) patients, no. | 0 | 0 |
| GOLD 2 (moderate) patients, no. | 0 | 8 |
| GOLD 3 (severe) patients, no. | 0 | 0 |
| GOLD 4 (very severe) patients, no. | 0 | 0 |
| Receiving inhaled steroids, no. | 0 | 3 |
| Receiving theophyllines, no. | 0 | 0 |
| Receiving long-acting b2-agonist, no. | 0 | 6 |
| Receiving anticholinergics, no. | 0 | 7 |

COPD: chronic obstructive pulmonary disease;
FEV1: forced expiratory volume in one second;
FVC: forced vital capacity;
Pack-yr = 1 year smoking 20 cigarettes-day.
Data are mean ± SE.

Peripheral neutrophils and monocytes as well as whole blood were obtained from 8 patients with COPD, defined according to GOLD guidelines and 7 healthy subjects. Patients were aged 65.1±14 years, FEV1 58.2±3% predicted. All patients were current smokers. There were no exacerbations of the disease within 2 weeks prior to taking blood samples.

7 age-matched non-smoking control subjects with normal lung function (age 66.1±6 years old, FEV1 98±3% predicted) who did not have any respiratory disease, were also recruited as normal controls, respectively. Routine lung function tests were performed to evaluate forced vital capacity (FVC), forced expiratory volume in 1 s (FEV1) and FEV1/FVC ratio using a Vitalograph® alpha III spirometer (Vitalograph, Maids Moreton, UK). This project was approved by the local ethics committee of General University Hospital, Valencia, Spain, and written informed consent was taken from each patient or volunteer before starting blood sampling and lung function testing.

B. Isolation of Human Neutrophils

Neutrophils were isolated from peripheral venous blood by standard laboratory procedures. In brief, peripheral venous blood was mixed with dextran 500 at 3% (in 0.9% saline) in a proportion of 2:1. This mixture was incubated at room temperature for 30 min until erythrocytes were sedimented. The upper phase was carefully collected and added on Ficoll-Paque Histopaque 1077 (Amershan Pharmacia Biotech, Barcelona, Espana) density gradient in a proportion of 3:1. The two phases generated were centrifuged at 150 g, 4° C. for 30 min. Thus, the pellet obtained (which is consisted a mixture of neutrophils and low proportion of residual erythrocytes and traces of eosinophils and basophils) was resuspended in an erythrocyte lysis buffer (Biolegend, UK) for 5 min in ice. Cell suspension was washed two times with phosphate buffer (PBS). The preparations were >97% pure in neutrophils as assessed by Giemsa staining, and had a viability of >99%, measured by trypan blue exclusion. Neither purity nor viability was affected in the study's different experimental conditions.

C. Preparation of Cigarette Smoke Extract solutions

CSE was prepared as follows: Briefly, the smoke of a research cigarette (2R4F; Tobacco Health Research, University of Kentucky, KY, USA) was generated by a respiratory pump (Apparatus Rodent Respirator 680; Harvard, Germany) through a puffing mechanism related to the human smoking pattern (3 puff/min; 1 puff 35 ml; each puff of 2 s duration with 0.5 cm above the filter) and was bubbled into a flask containing 25 ml of pre-warmed (37° C.) Roswell Park Memorial Institute (RPMI)-1640 culture medium. The CSE solution was sterilized by filtration through a 0.22-μm cellulose acetate sterilizing system (Corning, N.Y.). The resultant CSE solution was considered to be 100% CSE and was used for experiments within 30 min of preparation. CSE 10% corresponds approximately to the exposure associated with smoking two packs per day. The quality of the prepared CSE solution was assessed based on the absorbance at 320 nm, which is the specific absorption wavelength of peroxynitrite. Stock solutions with an absorbance value of 3.0±0.1 were used. To test for cytotoxicity from CSE, isolated neutrophils were treated with CSE concentrations of up to 5% for 24. No significant difference in the lactate dehydrogenase supernatant level (lactate dehydrogenase cytotoxicity assay; Cayman, Spain) was observed in comparison with the control group (data not shown).

Example 6

Assay: Effect of Compound A, dexamethasone and combination thereof on secretion of inflammatory marker IL-8 induced by CSE in peripheral blood neutrophils from healthy non-smokers and COPD smoker patients.

Isolated human neutrophils from healthy volunteers and COPD patients were incubated with Compound A (0.01 nM-100 μM) and Dexamethasone (0.1 nM-1 μM) or vehicle for 30 minutes before incubation with or without CSE 5% for 6 hours in standard cell culture conditions (37° C. and 5% $CO_2$). Supernatants were collected to measure different inflammatory markers.

IL-8 was measured by ELISA using a commercially available kit.

Experiments were done in triplicate in almost three patients per experimental condition.

Figure 4:
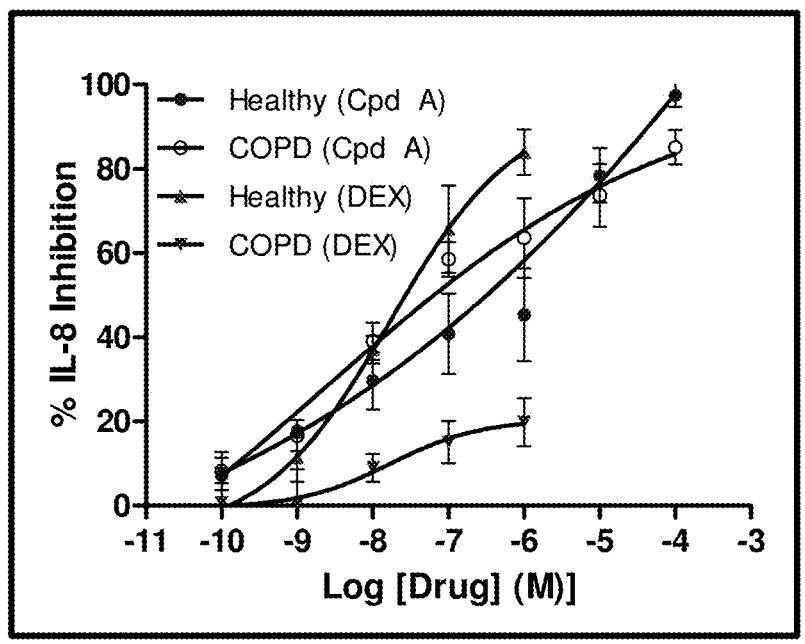
FIG. 4 is a bar graph depicting the IL-8 concentration-dependent inhibitory curve for neutrophils from healthy and COPD patients stimulated with CSE 5% in the presence of Compound A (0.01 nM-100 μM) or dexamethasone according to the procedure in Example 6.

Neutrophils from healthy and COPD patients were stimulated with CSE 5% in the presence of Compound A (0.01 nM-100 μM) or dexamethasone (DEX; 0.1 nM-1 μM) for 6 h and IL-8 supernatants were measured. Concentration-dependent inhibitory curves are shown in FIG. 4 and in Table 3.

Compound A concentration-dependently inhibited IL-8 secretion in neutrophils from healthy and COPD patients with a maximal percent inhibition of 97.4±5.3% and 85.14±8.24% respectively. As a reference, the anti-inflammatory dexamethasone showed a favorable inhibitory profile on CSE-induced IL-8 release only in neutrophils from Healthy patients with a maximal percent inhibition of 83.9±10%. However in neutrophils from COPD patients, dexamethasone was not able to significantly inhibit IL-8 release showing a corticosteroid insensitive profile.

Example 7

Assay: Effect of Compound A on basal RNA expression of corticosteroid resistance mediators and PI3K isoforms using peripheral blood neutrophils from healthy non-smokers and COPD smoker patients Measurement of Basal RNA Expression of Corticosteroid Resistant Mediators:

Total RNA was isolated from peripheral human neutrophils from COPD patients in basal conditions and after experimental conditions. Cells were homogenized and RNA was extracted using TriPure® Isolation Reagent (Roche, Indianapolis, USA). The reverse transcription was performed in 300 ng of total RNA with TaqMan reverse transcription reagents kit (Applied Biosystems, Perkin-Elmer Corporation, CA, USA). 1.5 μl of result cDNA was amplified with specific predesigned primers (Applied Biosystems) for MIF (cat no Hs00236988), MKP-1 (cat no Hs00610256), PI3K-δ (cat no Hs00192399), PI3Kγ (cat no Hs00277090) and GAPDH (cat no 4310884E) as endogenous control in a 7900HT Fast Real-Time PCR System (Applied Biosystem) using Universal Master Mix (Applied Biosystems). Relative quantification of these different transcripts was determined with the $2^{-\Delta\Delta Ct}$ method and normalized to control groups.

mRNA expression of the MIF, MKP-1, PI3K-δ and PI3Kγ genes was measured in basal conditions and at the end of the experiments.

Experiments were done in triplicate in at least three patients per experimental condition.

TABLE 3

Table 3. Inhibition of IL-8 release in isolated peripheral blood neutrophils from healthy (N = 3) and COPD patients (N = 3). Inhibitory concentration-dependent curves were generated by incubation with Compound A (Cpd A; 0.01 nM-100 μM) or Dexamethasone (DEX; 0.1 nM-1 μM) in response to cigarette smoke extract (CSE 5%). Values are mean ± SEM of 3 independent experiments run in triplicate. $IC_{50}$ values for half-maximum inhibition were calculated by nonlinear regression analysis.

| Stimulus CSE 5% | HEALTHY | | | COPD | | |
|---|---|---|---|---|---|---|
| | Maximal % Inhibition | $-\log IC_{50}$ | N | Maximal % Inhibition | $-\log IC_{50}$ | N |
| Cpd A | 97.4 ± 5.3 | 6.53 ± 0.22 | 3 | 85.14 ± 8.24 | 7.32 ± 0.21 | 3 |
| DEX | 83.9 ± 10.7 | 7.85 ± 0.17 | 3 | 19.84 ± 11.46* | 7.87 ± 0.78 | 3 |

*p < 0.05 vs Healthy values.

Figure 5:
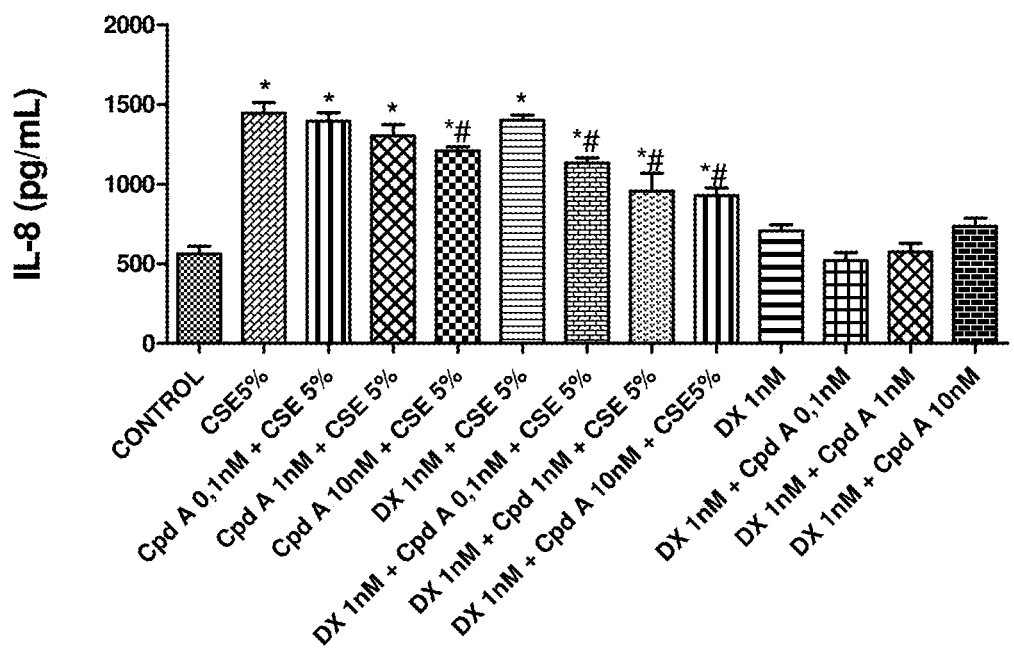
FIG. 5 is a bar graph depicting inhibition of CSE-induced IL-8 release in neutrophils from COPD patients by addition of a fixed concentration of dexamethasone 1 nM to concentrations of Compound A of 0.1 nM, 1 nM, and 10 nM according to the procedure in Example 6.

The addition of a fixed concentration of dexamethasone 1 nM to increasing concentrations of Compound A of 0.1 nM, 1 nM, and 10 nM, showed increases in inhibiting CSE-induced IL-8 release in neutrophils from COPD patients (FIG. 5).

Figure 6:
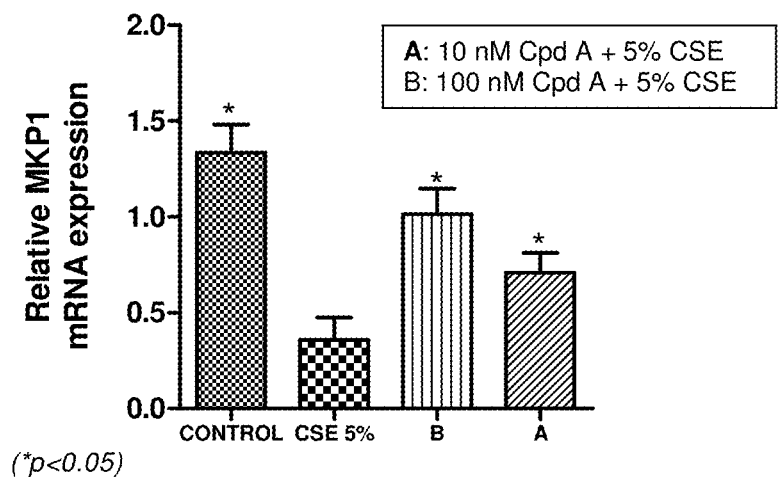
FIG. 6 is a bar graph depicting relative MKP1 mRNA expression stimulated with CSE 5% alone or in the presence of 10 nM or 100 nM of Compound A according to the procedure in Example 7.
Figure 7:
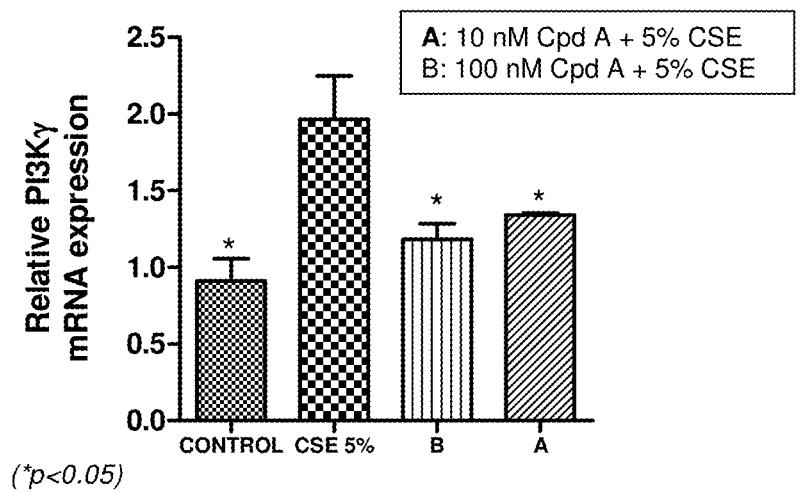
FIG. 7 is a bar graph depicting relative PI3Kγ mRNA expression stimulated with CSE 5% alone or in the presence of 10 nM or 100 nM of Compound A according to the procedure in Example 7.

Results:

The expression of MIF was not significantly affected by CSE or Compound A exposure. In contrast, CSE decreased the expression of MKP1 to approximately 0.4-fold of control. Compound A increased the expression of MKP1 near to control levels which correlates well with the inhibitory effect of Compound A on IL-8 release. See FIG. 6. While PI3Kδ was not affected by CSE treatment, administration of Compound A caused a significant reduction in CSE induced PI3Kγ expression (FIG. 7).

Example 8

Assay: Effect of Compound A, Dexamethasone and combination thereof on basal expression of PI3K isoforms using peripheral blood neutrophils from healthy non-smokers and COPD smoker patients.

Measurement of Pi3K Isoforms:

To measure PI3K activity, neutrophils from COPD patients were isolated and incubated with Compound A at 10 nM for 1 h. Then cells were stimulated with CSE 5% for 30 min. After cell stimulation, neutrophils were centrifuged and total protein was extracted from neutrophils. Total protein amount was measured using The Bio-Rad assay (Bio-Rad Laboratories Ltd., Herts, UK) to ensure equal amount. PI3K activity was measured using the PI3-Kinase Activity ELISA: Pico (cat. no k-1000 s, Echelon Bioscience, Salt Lake City, USA) according to the manufacturer's protocol. In brief, PI3-K reactions were run with the Class I PI3-K physiological substrate PI(4,5)P2 (PIP2). The enzyme reactions, PIP3 standards and controls were then mixed and incubated with PIP3 binding protein that is highly specific and sensitive to PIP3. This mixture was then transferred to a PIP3-coated microplate for competitive binding. Afterwards, a peroxidase-linked secondary detector and colorimetric detection was used to detect the amount of PIP3 produced by PI3-K through comparing the enzyme reactions with a PIP3 standard curve.

Experiments were done in triplicate in at least three patients per experimental condition.

Figure 8:
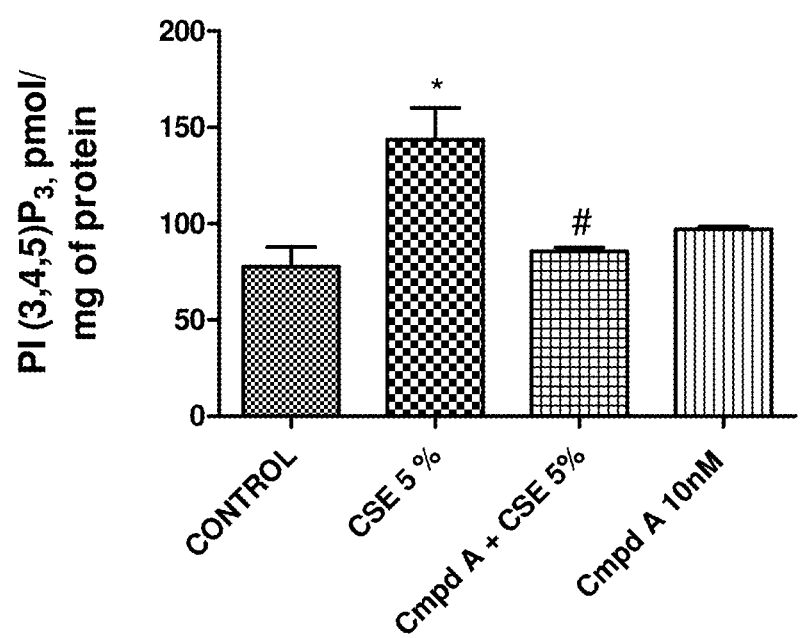
FIG. 8 is a bar graph depicting PIP3 production in the presence of CSE 5% alone, CSE5% and 10 nM of Compound A, or 10 nM of Compound A alone.

Results:

In neutrophils from COPD patients, CSE 5% increased the PI3K activity measured as PIP3 production. The addition of Compound A at 10 nM completely suppressed the PI3K activity (FIG. 8).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications, patents and patent applications cited in this application are herein incorporated by reference to the same extent as if each individual publication, patent or patent application was specifically and individually indicated to be incorporated herein by reference.

We claim:

1. A method of treating a respiratory disease or condition selected from asthma, allergic rhinitis and chronic obstructive pulmonary disease, the method comprising administering to a subject in need thereof a therapeutically effective amount of (i) a dual PI3K delta and gamma inhibitor of formula A:

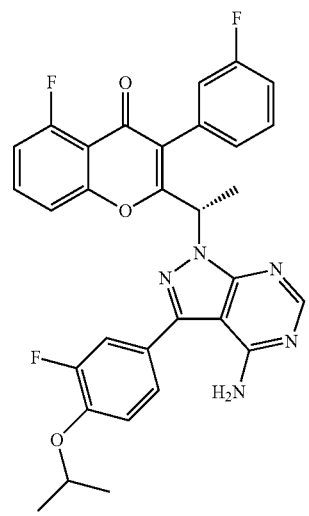

Formula A or a pharmaceutically acceptable salt thereof, and (ii) mometasone furoate, fluticasone, fluticasone propionate, or a pharmaceutically acceptable salt thereof.

2. The method according to claim 1, wherein the therapeutically effective amount of (i) the dual PI3K delta and gamma inhibitor, and the therapeutically effective amount of (ii) the mometasone furoate, fluticasone, fluticasone propionate, or a pharmaceutically acceptable salt thereof are administered simultaneously as a combined formulation.

3. The method according to claim 1, wherein the therapeutically effective amount of (i) the dual PI3K delta and gamma inhibitor, and the therapeutically effective amount of (ii) the mometasone furoate, fluticasone, fluticasone propionate, or a pharmaceutically acceptable salt thereof are administered sequentially.

4. The method according to claim 3, wherein the therapeutically effective amount of the mometasone furoate, fluticasone, fluticasone propionate, or a pharmaceutically acceptable salt thereof is administered before the therapeutically effective amount of the dual PI3K delta and gamma inhibitor.

5. The method according to claim 1, wherein the therapeutically effective amount of the dual PI3K delta and gamma inhibitor is administered twice daily to once every three weeks, and the therapeutically effective amount of the mometasone furoate, fluticasone, fluticasone propionate, or a pharmaceutically acceptable salt thereof is administered twice daily to once every three weeks.

6. The method according to claim 1, wherein the dual PI3K delta and gamma inhibitor and the mometasone furoate, fluticasone, fluticasone propionate, or a pharmaceutically acceptable salt thereof are each administered in an amount ranging from about 0.01 mg to about 1000 mg.

7. The method of claim 1, wherein the dual PI3K delta and gamma inhibitor and the mometasone furoate, fluticasone, fluticasone propionate, or a pharmaceutically acceptable salt thereof are administered at a ratio of about 1:100 to about 100:1 by weight.

8. The method according to claim 1, wherein the respiratory disease or condition is asthma.

9. The method according to claim 1, wherein the respiratory disease or condition is allergic rhinitis.

10. The method according to claim 1, wherein the respiratory disease or condition is chronic obstructive pulmonary disease.

11. The method of claim 1, wherein the method comprises administering a therapeutically effective amount of (i) a dual PI3K delta and gamma inhibitor of formula A:

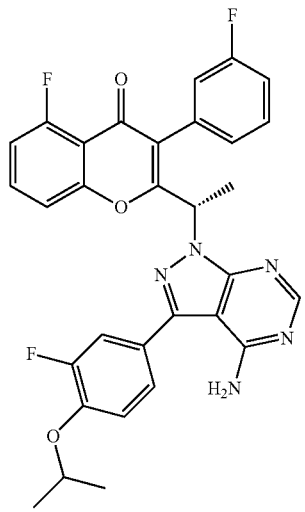

Formula A or a pharmaceutically acceptable salt thereof, and (ii) mometasone furoate or a pharmaceutically acceptable salt thereof.

12. The method of claim 11, wherein the method comprises administering a therapeutically effective amount of (i) a dual PI3K delta and gamma inhibitor of formula A:

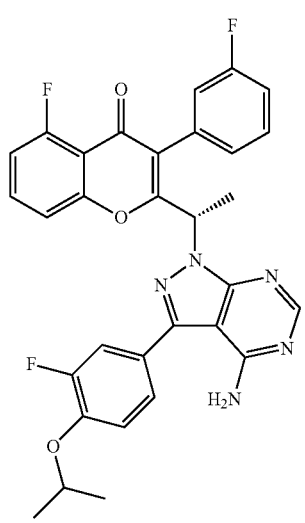

Formula A or a pharmaceutically acceptable salt thereof, and (ii) mometasone furoate.

13. The method of claim 1, wherein the method comprises administering a therapeutically effective amount of (i) a dual PI3K delta and gamma inhibitor of formula A:

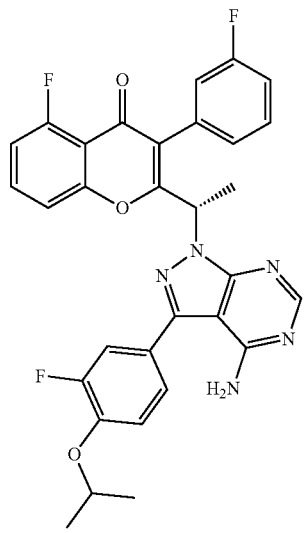

Formula A or a pharmaceutically acceptable salt thereof, and (ii) fluticasone or a pharmaceutically acceptable salt thereof.

14. The method of claim 13, wherein the method comprises administering a therapeutically effective amount of (i) a dual PI3K delta and gamma inhibitor of formula A:

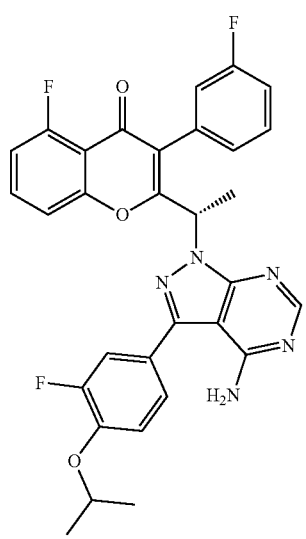

Formula A or a pharmaceutically acceptable salt thereof, and (ii) fluticasone.

15. The method of claim 1, wherein the method comprises administering a therapeutically effective amount of (i) a dual PI3K delta and gamma inhibitor of formula A:

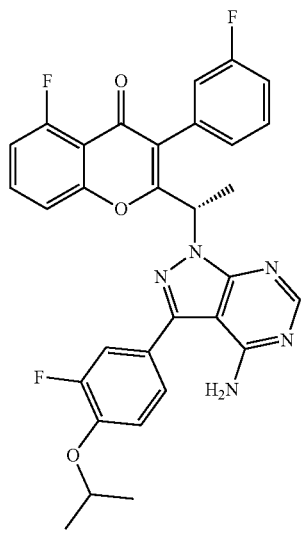

Formula A or a pharmaceutically acceptable salt thereof, and (ii) fluticasone propionate or a pharmaceutically acceptable salt thereof.

16. The method of claim 15, wherein the method comprises administering a therapeutically effective amount of (i) a dual PI3K delta and gamma inhibitor of formula A:

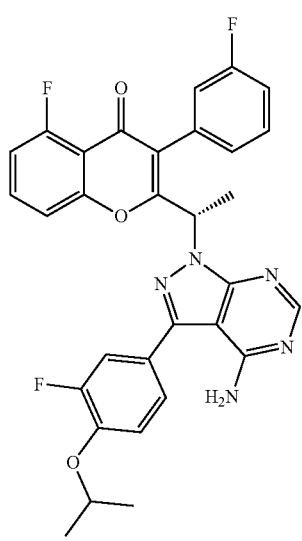

Formula A or a pharmaceutically acceptable salt thereof, and (ii) fluticasone propionate.

17. The method according to claim 11, wherein the respiratory disease or condition is asthma.

18. The method according to claim 11, wherein the respiratory disease or condition is allergic rhinitis.

19. The method according to claim 11, wherein the respiratory disease or condition is chronic obstructive pulmonary disease.

20. A method of treating a respiratory disease or condition selected from asthma, allergic rhinitis and chronic obstructive pulmonary disease, the method comprising intranasally administering to a subject in need thereof a therapeutically effective amount of (i) a dual PI3K delta and gamma inhibitor of formula A:

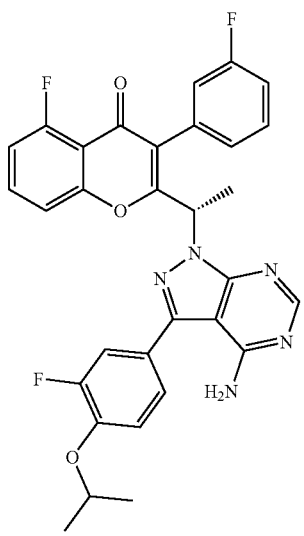

Formula A or a pharmaceutically acceptable salt thereof, and (ii) mometasone furoate or a pharmaceutically acceptable salt thereof.

21. The method according to claim 20, wherein the respiratory disease or condition is asthma.

22. The method according to claim 20, wherein the respiratory disease or condition is allergic rhinitis.

23. The method according to claim 20, wherein the respiratory disease or condition is chronic obstructive pulmonary disease.

24. A method of treating a respiratory disease or condition selected from asthma, allergic rhinitis and chronic obstructive pulmonary disease, the method comprising intranasally administering to a subject in need thereof a therapeutically effective amount of (i) a dual PI3K delta and gamma inhibitor of formula A:

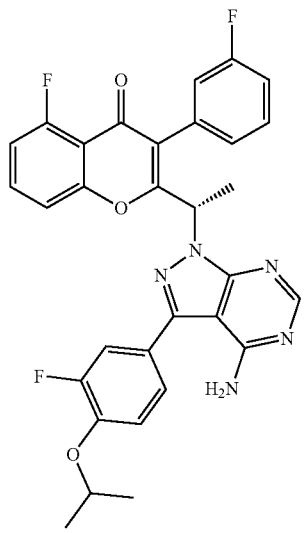

Formula A or a pharmaceutically acceptable salt thereof, and (ii) fluticasone or a pharmaceutically acceptable salt thereof.

25. The method according to claim 24, wherein the respiratory disease or condition is asthma.

26. The method according to claim 24, wherein the respiratory disease or condition is allergic rhinitis.

27. The method according to claim 24, wherein the respiratory disease or condition is chronic obstructive pulmonary disease.

28. A method of treating a respiratory disease or condition selected from asthma, allergic rhinitis and chronic obstructive pulmonary disease, the method comprising intranasally administering to a subject in need thereof a therapeutically effective amount of (i) a dual PI3K delta and gamma inhibitor of formula A:

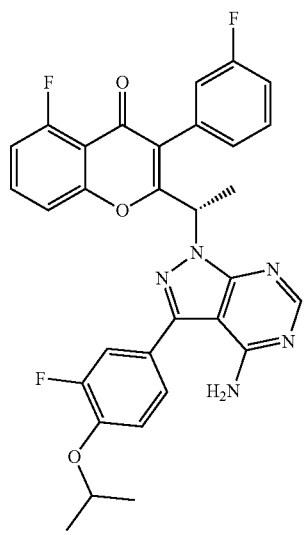

Formula A or a pharmaceutically acceptable salt thereof, and (ii) fluticasone propionate or a pharmaceutically acceptable salt thereof.

29. The method according to claim 28, wherein the respiratory disease or condition is asthma.

30. The method according to claim 28, wherein the respiratory disease or condition is allergic rhinitis.

31. The method according to claim 28, wherein the respiratory disease or condition is chronic obstructive pulmonary disease.

* * * * *